United States Patent
Scirica et al.

(10) Patent No.: US 8,657,177 B2
(45) Date of Patent: Feb. 25, 2014

(54) SURGICAL APPARATUS AND METHOD FOR ENDOSCOPIC SURGERY

(75) Inventors: Paul A. Scirica, Huntington, CT (US); Ernest Aranyi, Easton, CT (US); Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 288 days.

(21) Appl. No.: 13/280,859

(22) Filed: Oct. 25, 2011

(65) Prior Publication Data
US 2013/0098969 A1  Apr. 25, 2013

(51) Int. Cl.
*A61B 17/068* (2006.01)

(52) U.S. Cl.
USPC .................. 227/180.1; 227/19; 227/176.1

(58) Field of Classification Search
USPC ............... 227/19, 175.1, 175.2, 176.1, 178.1, 227/180.1; 606/139, 153, 219
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |

(Continued)

FOREIGN PATENT DOCUMENTS

| | | |
|---|---|---|
| EP | 0634144 A1 | 1/1995 |
| EP | 1690502 A1 | 8/2006 |

(Continued)

OTHER PUBLICATIONS

European Search Report corresponding to European Application EP 10 25 2037.6; completed Mar. 1, 2011 and mailed Mar. 9, 2011; 3 pages.

(Continued)

*Primary Examiner* — Scott A. Smith

(57) ABSTRACT

The present disclosure is directed to an endoscopic surgical instrument and methods for performing a diverticulum treatment. The surgical instrument includes a handle assembly, an elongated member and a jaw assembly. The elongated member is operably coupled to the distal end of the handle assembly, while the jaw assembly is operably coupled to a distal end of the elongated member. The jaw assembly includes a knife slot that is defined therewithin and is adapted to receive a knife blade to thereby cut tissue that is disposed between the jaw assembly. The jaw assembly is configured to approximate an esophageal tract and a diverticulum.

24 Claims, 14 Drawing Sheets

(56) References Cited

U.S. PATENT DOCUMENTS

| | | | |
|---|---|---|---|
| 5,413,267 A | 5/1995 | Solyntjes et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,542,594 A | 8/1996 | McKean et al. | |
| 5,562,239 A | 10/1996 | Boiarski et al. | |
| 5,653,374 A | 8/1997 | Young et al. | |
| 5,667,517 A | 9/1997 | Hooven | |
| 5,704,534 A | 1/1998 | Huitema et al. | |
| 5,713,505 A | 2/1998 | Huitema | |
| 5,779,130 A | 7/1998 | Alesi et al. | |
| 5,782,396 A * | 7/1998 | Mastri et al. | 227/175.3 |
| 5,782,397 A | 7/1998 | Koukline | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,017,354 A | 1/2000 | Culp et al. | |
| 6,032,849 A * | 3/2000 | Mastri et al. | 227/176.1 |
| 6,045,560 A | 4/2000 | McKean et al. | |
| 6,090,123 A | 7/2000 | Culp et al. | |
| 6,129,547 A | 10/2000 | Cise et al. | |
| 6,241,139 B1 * | 6/2001 | Milliman et al. | 227/175.1 |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,434,507 B1 | 8/2002 | Clayton et al. | |
| 6,443,973 B1 | 9/2002 | Whitman | |
| 6,459,822 B1 | 10/2002 | Hathaway et al. | |
| 6,461,372 B1 | 10/2002 | Jensen et al. | |
| 6,471,637 B1 | 10/2002 | Green et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,792,390 B1 | 9/2004 | Burnside et al. | |
| 6,817,508 B1 | 11/2004 | Racenet et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 * | 1/2006 | Mastri et al. | 227/176.1 |
| 7,032,798 B2 | 4/2006 | Whitman et al. | |
| 7,055,731 B2 | 6/2006 | Shelton, IV et al. | |
| 7,077,856 B2 | 7/2006 | Whitman | |
| 7,111,769 B2 | 9/2006 | Wales et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,225,964 B2 * | 6/2007 | Mastri et al. | 227/176.1 |
| 7,246,734 B2 | 7/2007 | Shelton, IV | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 * | 8/2008 | Shelton et al. | 227/180.1 |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,481,347 B2 | 1/2009 | Roy | |
| 7,487,899 B2 | 2/2009 | Shelton, IV et al. | |
| 7,549,564 B2 | 6/2009 | Boudreaux | |
| 7,565,993 B2 * | 7/2009 | Milliman et al. | 227/175.1 |
| 7,568,603 B2 | 8/2009 | Shelton, IV et al. | |
| 7,588,176 B2 | 9/2009 | Timm et al. | |
| 7,637,409 B2 | 12/2009 | Marczyk | |
| 7,641,093 B2 | 1/2010 | Doll et al. | |
| 7,644,848 B2 | 1/2010 | Swayze et al. | |
| 7,670,334 B2 | 3/2010 | Hueil et al. | |
| 7,673,780 B2 | 3/2010 | Shelton, IV et al. | |
| 7,721,931 B2 | 5/2010 | Shelton, IV et al. | |
| 7,740,159 B2 | 6/2010 | Shelton, IV et al. | |
| 7,743,960 B2 | 6/2010 | Whitman et al. | |
| 7,758,613 B2 | 7/2010 | Whitman | |
| 7,766,210 B2 | 8/2010 | Shelton, IV et al. | |
| 7,770,773 B2 | 8/2010 | Whitman et al. | |
| 7,770,775 B2 | 8/2010 | Shelton, IV et al. | |
| 7,793,812 B2 * | 9/2010 | Moore et al. | 227/176.1 |
| 7,799,039 B2 | 9/2010 | Shelton, IV et al. | |
| 7,802,712 B2 | 9/2010 | Milliman et al. | |
| 7,845,537 B2 | 12/2010 | Shelton, IV et al. | |
| 7,857,185 B2 * | 12/2010 | Swayze et al. | 227/175.2 |
| 7,905,897 B2 | 3/2011 | Whitman et al. | |
| 7,918,230 B2 | 4/2011 | Whitman et al. | |
| 7,947,034 B2 | 5/2011 | Whitman | |
| 7,951,071 B2 | 5/2011 | Whitman et al. | |
| 7,959,051 B2 * | 6/2011 | Smith et al. | 227/176.1 |
| 7,963,433 B2 | 6/2011 | Whitman et al. | |
| 7,967,178 B2 | 6/2011 | Scirica et al. | |
| 7,992,758 B2 | 8/2011 | Whitman et al. | |
| 8,016,855 B2 | 9/2011 | Whitman et al. | |
| 8,020,743 B2 | 9/2011 | Shelton, IV | |
| 8,157,151 B2 | 4/2012 | Ingmanson et al. | |
| 8,186,555 B2 | 5/2012 | Shelton, IV et al. | |
| 8,220,367 B2 | 7/2012 | Hsu | |
| 8,241,322 B2 | 8/2012 | Whitman et al. | |
| 8,292,888 B2 | 10/2012 | Whitman | |
| 8,357,144 B2 | 1/2013 | Whitman et al. | |
| 8,365,972 B2 | 2/2013 | Aranyi et al. | |
| 8,372,057 B2 | 2/2013 | Cude et al. | |
| 8,391,957 B2 | 3/2013 | Carlson et al. | |
| 2003/0130677 A1 | 7/2003 | Whitman et al. | |
| 2004/0111012 A1 | 6/2004 | Whitman | |
| 2006/0025816 A1 | 2/2006 | Shelton | |
| 2006/0142656 A1 | 6/2006 | Malackowski et al. | |
| 2007/0023477 A1 | 2/2007 | Whitman et al. | |
| 2007/0029363 A1 | 2/2007 | Popov | |
| 2007/0084897 A1 | 4/2007 | Shelton et al. | |
| 2007/0102472 A1 | 5/2007 | Shelton | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0185419 A1 | 8/2008 | Smith et al. | |
| 2008/0208195 A1 | 8/2008 | Shores et al. | |
| 2008/0251561 A1 | 10/2008 | Eades et al. | |
| 2008/0255607 A1 | 10/2008 | Zemlok | |
| 2008/0262654 A1 | 10/2008 | Omori et al. | |
| 2009/0090763 A1 | 4/2009 | Zemlok et al. | |

(56) References Cited

U.S. PATENT DOCUMENTS

| | | |
|---|---|---|
| 2009/0095790 A1 | 4/2009 | Whitman et al. |
| 2009/0099876 A1 | 4/2009 | Whitman |
| 2009/0101692 A1 | 4/2009 | Whitman et al. |
| 2009/0145947 A1 | 6/2009 | Scirica et al. |
| 2009/0179063 A1 | 7/2009 | Milliman et al. |
| 2009/0182193 A1 | 7/2009 | Whitman et al. |
| 2009/0209990 A1 | 8/2009 | Yates et al. |
| 2011/0121049 A1 | 5/2011 | Malinouskas et al. |
| 2011/0218522 A1 | 9/2011 | Whitman |
| 2011/0253765 A1 | 10/2011 | Nicholas et al. |
| 2011/0295242 A1 | 12/2011 | Spivey et al. |

FOREIGN PATENT DOCUMENTS

| | | |
|---|---|---|
| EP | 1736112 A1 | 12/2006 |
| EP | 1769754 A1 | 4/2007 |
| EP | 1 813 203 A2 | 8/2007 |
| EP | 1943958 A1 | 7/2008 |
| EP | 1943976 A2 | 7/2008 |
| EP | 2027819 A1 | 2/2009 |
| EP | 2055243 A2 | 5/2009 |
| EP | 2098170 A2 | 9/2009 |
| EP | 2100561 A2 | 9/2009 |
| EP | 2 236 098 | 10/2010 |
| EP | 2 263 568 | 12/2010 |
| WO | 00/72760 A1 | 12/2000 |
| WO | 00/72765 A1 | 12/2000 |
| WO | 03/000138 A2 | 1/2003 |
| WO | 03/026511 A1 | 4/2003 |
| WO | 03/077769 A1 | 9/2003 |
| WO | 2004/107989 A1 | 12/2004 |
| WO | 2006/042210 A2 | 4/2006 |
| WO | WO 2007/014355 A2 | 2/2007 |
| WO | 2007/026354 A1 | 3/2007 |
| WO | 2008/131362 A2 | 10/2008 |
| WO | 2008/133956 A2 | 11/2008 |
| WO | WO 2009/039506 A1 | 3/2009 |
| WO | 2009/132359 A2 | 10/2009 |

OTHER PUBLICATIONS

European Search Report for EP 12186177.7 date of completion is Jan. 30, 2013 (6 pages).

Extended European Search Report corresponding to EP 13 16 3033.7, completed Jun. 27, 2013, and dated Jul. 15, 2013; (8 pp).

International Search Report from the corresponding EP Application No. 12186177.7 dated Aug. 23, 2013.

International Search Report corresponding to PCT/US2005/027266, completed May 30, 2008 and mailed Jun. 18, 2008; (2 pp.).

Extended European Search Report corresponding to EP 08 25 3184.9, completed Feb. 12, 2009 and mailed Feb. 27, 2009; (3 pp.).

Extended European Search Report corresponding to EP 10 25 0228.3, completed May 20, 2010 and mailed Jun. 1, 2010; (6 pp.).

Extended European Search Report corresponding to EP 10 25 1968.3, completed on Jul. 4, 2011 and mailed Jul. 14, 2011; (12 pp.).

Extended European Search Report corresponding to EP 11 15 2266.0, completed Jul. 15, 2011 and mailed Jul. 28, 2011; (3 pp.).

Extended European Search Report corresponding to EP 11 25 0462.6, completed Jul. 20, 2011 and mailed Jul. 28, 2011; (6 pp.).

Extended European Search Report corresponding to EP 11 25 0771.0, completed Feb. 7, 2012 and mailed Feb. 17, 2012; (3 pp.).

Extended European Search Report corresponding to EP 06 78 8914.7, completed May 3, 2012 and mailed May 11, 2012; (8 pp.).

Extended European Search Report corresponding to EP 08 25 2703.7, completed Oct. 23, 2008 and mailed Oct. 31, 2008; (7 pp.).

\* cited by examiner

SURGICAL APPARATUS AND METHOD FOR ENDOSCOPIC SURGERY

BACKGROUND

1. Technical Field

The present disclosure relates to an apparatus and method of performing a surgical procedure. More particularly, the present disclosure relates to an apparatus and method for performing a minimally invasive surgical procedure utilizing a motor driven instrument.

2. Background of Related Art

In certain conventional surgical procedures, surgeons have direct access to the operative site. However, laparoscopic surgery, a type of minimally invasive surgery, has been developed, in which the surgical site is viewed through a laparoscope or endoscope and the instruments are introduced through a trocar cannula. The benefits of laparoscopic surgery include reduced hospital stay, speedier recovery, and less pain.

One of the instruments utilized in laparoscopic surgery, as well as other types of minimally invasive surgery, is the surgical stapler. Surgical stapling devices are employed by surgeons to sequentially or simultaneously apply one or more rows of fasteners, e.g., staples or two-part fasteners, to body tissue for the purpose of joining segments of body tissue together. Such devices generally consist of a pair of jaws or finger-like structures between which the body tissue to be joined is placed. When the stapling device is actuated, or "fired", a firing member or members contact staple drive members in one of the jaws. The staple drive members push the surgical staples through the body tissue and into an anvil in an opposite jaw which crimps the staples closed. If tissue is to be removed or separated, a knife blade can be provided in the jaws of the device to cut the tissue between the lines of staples.

Certain surgical device manufacturers have developed surgical instruments that are not manually actuated by, for example, a pivotable, manually graspable handle part, but are driven by a motor either provided in a separate housing, or provided in the handle of the instrument. Certain electromechanical surgical devices include a handle assembly, which is reusable and connectable with a replaceable loading unit prior to use. Then, following the use of the instrument, the loading unit is disconnected from the handle assembly, in order to be disposed of. A system including reusable portions has the potential advantage of reducing the cost of the instrument, as a portion of the instrument is reused over time. In addition, the replaceable parts can be offered in multiple different configurations, which can include, for surgical staplers, staples lines of various lengths, staple sizes of various lengths, etc.

Many of these electromechanical surgical devices are relatively expensive to manufacture, purchase and/or operate. There is a desire by manufactures and end users to develop electromechanical surgical devices that are relatively inexpensive to manufacture, purchase and/or operate.

Accordingly, a need exists for electromechanical surgical apparatus, devices and/or systems that are relatively economical to develop and manufacture, to store and ship, as well as economical and convenient to purchase and use from the end user's perspective.

There is also a need to provide flexibility for the user of such instruments, so as to provide the user with various parts that can be replaced, and various configurations to choose from.

SUMMARY

The present disclosure relates to an endoscopic surgical instrument, which includes various types of instrumentation.

In an aspect of the present application, a surgical instrument comprises a handle assembly including a housing; an elongated body extending distally from the handle assembly; and a jaw assembly adjacent a distal end of the elongated body. The jaw assembly includes a cartridge assembly including a plurality of fasteners and a longitudinal slot defined therein; an anvil having a fastener forming surface thereon, the cartridge assembly and anvil being mounted for movement with respect to one another between an open position and a closed position in close cooperative alignment for clamping tissue; an actuation sled supported within the cartridge assembly, the actuation sled being movable to urge the plurality of fasteners from the cartridge; and a knife blade mounted to the actuation sled. The jaw assembly further includes a drive beam including a vertical support strut and a cam member supported on the vertical support strut, the cam member being positioned to translate relative to the anvil to maintain the anvil in the closed position during firing of the fasteners, the vertical support strut being positioned to abut the actuation sled; and a drive screw supported within the cartridge assembly, the drive screw having a threaded portion, wherein the drive beam is threadably coupled to the threaded portion of the drive screw such that rotation of the drive screw imparts longitudinal movement of the drive beam.

The surgical instrument may have a the knife blade that is pivotably mounted to the actuation sled for pivotable movement in relation to the sled between a concealed position in which the knife blade is disposed within the actuation sled and a raised position in which the knife blade extends through the longitudinal slot. The knife blade may have an actuating surface that is arranged to be contacted by the vertical support strut.

The drive screw may define a longitudinal axis and the drive shaft may be disposed off-axis in relation to the drive screw.

The jaw assembly may further include a mounting portion coupled to the cartridge assembly and the anvil, the anvil being pivotally mounted to the mounting portion for pivotal movement in relation to the cartridge.

The anvil may include a pair of actuating shoulders disposed at a proximal end thereof. The mounting portion may include a pair of biasing members biased against the actuating shoulders for pushing the anvil into the open position.

In certain preferred embodiments, the instrument further comprises a camera mounted on the at least one of the cartridge assembly and the anvil. The camera may be mounted on the anvil.

The jaw assembly of the instrument may be configured to be removably attached to a shaft. The shaft may be selected from the group consisting of: a rigid shaft, a flexible shaft, and a shaft having a rigid portion and an articulating portion.

In a further aspect of the present disclosure, a surgical instrument comprises a handle assembly including a housing and an actuator; an elongated body extending distally from the handle assembly; a motor disposed at least partially within the housing; an actuation shaft mechanically engaged with the motor; a jaw assembly adjacent a distal end of the elongated body. The jaw assembly includes a cartridge assembly including a plurality of fasteners and a longitudinal slot defined therein; an anvil having a fastener forming surface thereon, the cartridge assembly and anvil being mounted for pivotal movement with respect to one another between an open position and a closed position for clamping tissue; an actuation sled supported within the cartridge assembly, the actuation sled being movable to urge the plurality of fasteners from the cartridge; and a knife blade mounted to the actuation sled. The jaw assembly further includes a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled to translate the actuation sled; and a drive screw supported within the cartridge assembly, the drive screw having a threaded portion, wherein the drive beam is threadably coupled to the threaded portion of the drive screw such that rotation of the drive screw imparts longitudinal movement of the drive beam.

The knife blade may be is pivotally mounted to the sled for movement in relation to the sled between a concealed position in which the knife blade is disposed within the actuation sled and a raised position in which the knife blade extends through the longitudinal slot The jaw assembly may further include a mounting portion coupled to the cartridge assembly and the anvil, the anvil being pivotally mounted to the mounting portion for pivotal movement in relation to the cartridge. The anvil may include a pair of actuating shoulders disposed at a proximal end thereof. The mounting portion may include a pair of biasing members biased against the actuating shoulders for pushing the anvil into the open position.

The jaw assembly may further include a drive shaft disposed within the mounting portion, the drive shaft mechanically coupling the drive screw to the actuation shaft, wherein the drive shaft transfers rotational motion of the actuation shaft to the drive screw., and the drive shaft may be is coupled off-axis to the drive screw.

In certain preferred embodiments, a camera is mounted on the at least one of the cartridge assembly and the anvil. The camera may be mounted on the anvil.

The jaw assembly of the surgical instrument may be configured to be removably attached to a shaft. The shaft may be selected from the group consisting of: a rigid shaft, a flexible shaft, and a shaft having a rigid portion and an articulating portion.

In another aspect of the present disclosure, a jaw assembly comprises a cartridge assembly including a plurality of fasteners and a longitudinal slot defined therein; an anvil having a fastener forming surface thereon and pivotally mounted in relation to the cartridge assembly for pivotal movement between an open position having a distal end spaced from the cartridge assembly and a closed position in close cooperative alignment with the fastener cartridge; an actuation sled supported within the cartridge assembly, the actuation sled being movable to urge the plurality of fasteners from the cartridge; a knife blade pivotally mounted to the actuation sled for pivotal movement in relation to the sled between a closed position in which the knife blade is disposed within the actuation sled and a deployed position in which the knife blade extends through the longitudinal slot. The jaw assembly may also include a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled and the knife blade to translate the actuation sled and to pivot the knife blade from the closed position into the deployed position.

The jaw assembly may further comprise a drive screw supported within the cartridge assembly, the drive screw having a threaded portion, wherein the drive beam is threadably coupled to the threaded portion of the drive screw such that rotation of the drive screw imparts longitudinal movement of the drive beam, or may further comprise a drive shaft mechanically coupling the drive screw to an actuation shaft, wherein the drive shaft transfers rotational motion of the actuation shaft to the drive screw.

The drive shaft may be coupled off-axis to the drive screw.

The jaw assembly may further comprise a mounting portion coupled to the cartridge assembly and the anvil, the anvil being pivotally mounted to the mounting portion for pivotal movement in relation to the cartridge. The anvil may include a pair of actuating wings disposed at a proximal end thereof, the mounting portion includes a pair of biasing members biased against the actuating wings for pushing the anvil into the open position.

The jaw assembly may be configured to be removably attached to a shaft. The shaft may be selected from the group consisting of: a rigid shaft, a flexible shaft, and a shaft having a rigid portion and an articulating portion.

BRIEF DESCRIPTION OF THE DRAWINGS

The above and other aspects, features, and advantages of the present disclosure will become more apparent in light of the following detailed description when taken in conjunction with the accompanying drawings in which.

Figure 1:
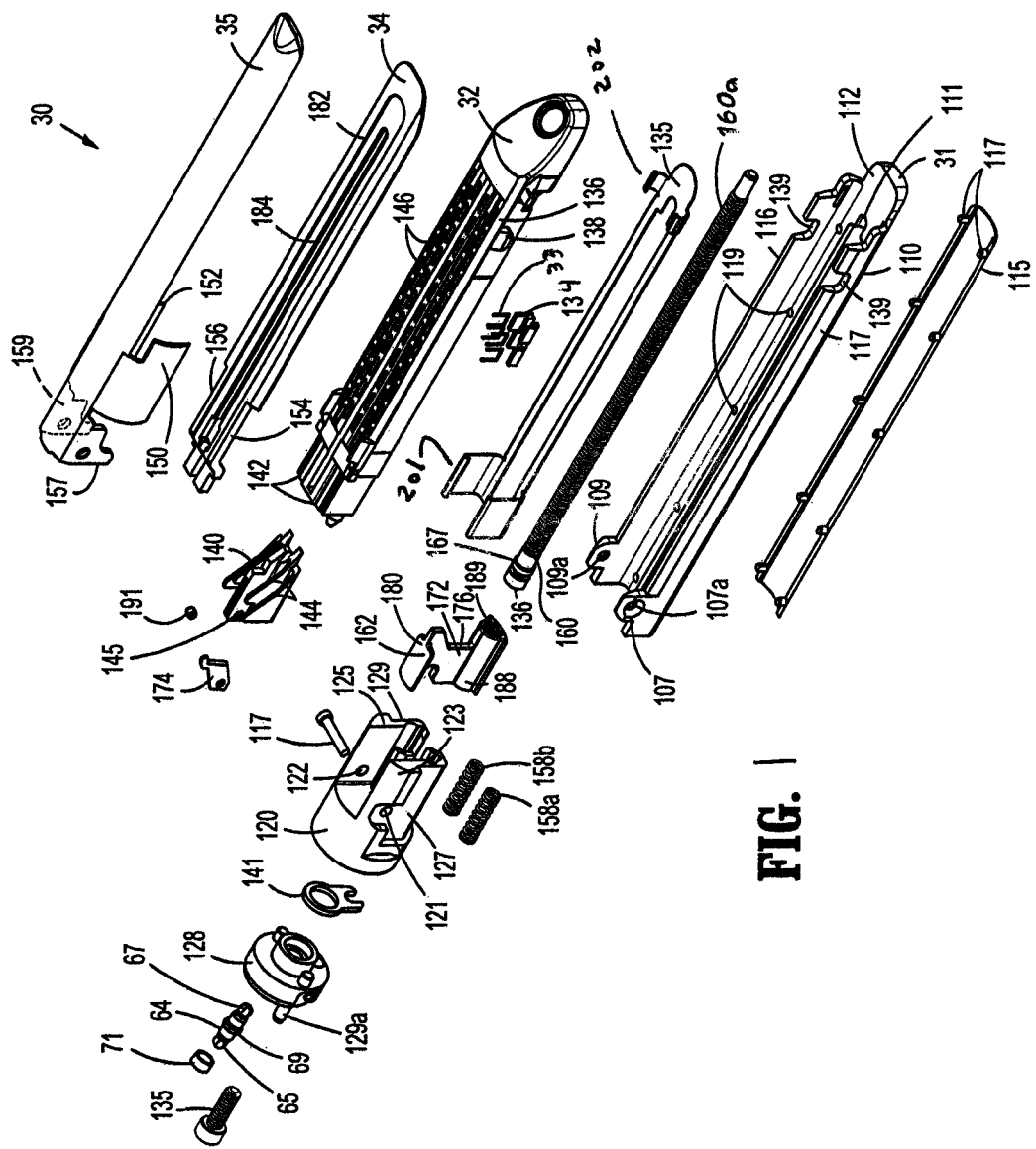
FIG. 1 is an exploded, perspective view of a jaw assembly for a surgical instrument in accordance with an embodiment of the present disclosure.

Other features of the present disclosure will become apparent from the following detailed description, taken in conjunction with the accompanying drawings, which illustrate, by way of example, the principles of the present disclosure.

DETAILED DESCRIPTION

Embodiments of the presently disclosed surgical devices are described in detail with reference to the drawings, in which like reference numerals designate identical or corresponding elements in each of the several views. As used herein, the term "distal" refers to that portion of the devices, or component thereof, that is farther from the user of the device, while the term "proximal" refers to that portion of the devices or component thereof, that is closer to the user.

Referring now to FIG. 1, a jaw assembly for an endoscopic instrument is shown. The jaw assembly, in certain embodiments disclosed herein, removably attached to an elongated shaft member that is integral with, or attached to the handle assembly of a surgical instrument. The elongated shaft member may be rigid, or flexible, or have rigid and flexible portions, or include one or more pivotable pivot members.

The elongated member may be articulated by the user of the instrument. In embodiments, the handle assembly and elongated member may include any suitable articulating mechanisms known in the art to manipulate (e.g., rotate and articulate) elongated member, which include, but not limited to gears, wires, cables, linkages, tubular shafts, drive rods, and combinations thereof.

The jaw assembly 30 includes a pair of jaw members. In certain embodiments, the jaw members include a staple cartridge assembly 32 and an anvil 34. Cartridge assembly 32 houses one or more staples or fasteners 33 that are disposed within the cartridge assembly, and is configured to deploy the one or more staples or fasteners 33 upon actuation of an actuator on the handle assembly. The cartridge assembly and the anvil are mounted so that they are movable with respect to one another. Anvil 34 in FIG. 1, for example, is movably (e.g., pivotally) mounted on the cartridge assembly and is movable between an open position, spaced apart from cartridge assembly 32, to a closed position wherein anvil 34 is in close cooperative alignment with cartridge assembly 32, to thereby clamp tissue. Alternatively, the cartridge assembly 32 may pivot with respect to the anvil member. The anvil 34 includes an inner fastener forming surface 39 having a plurality of fastener pockets (not shown) that are configured to receive fasteners 33 and to form fasteners 33 in a closed configuration when the fasteners are driven against the anvil 34.

During use, anvil 34 is moved between the open and closed positions by actuator. In embodiments, the actuator controls the rotational movement of an actuation shaft in the elongated shaft member, and the actuation shaft operates to rotate a drive screw 160 (see FIG. 1). The drive screw will interact with other members of the jaw assembly to move the anvil 34 between the open and closed positions. In this way, the jaw assembly can be operated to clamp onto tissue. Then, the drive screw 160 continues to rotate to move an actuation sled 140 (FIG. 1) provided in the jaw assembly. The sled moves distally through the cartridge assembly 32 to eject the fasteners 33 as described in more detail below.

The fasteners 33 are released from the cartridge assembly and they are configured to penetrate tissue that has been clamped between the jaw assembly, i.e., the cartridge assembly 32 and anvil 34 that have been approximated with one another. In certain preferred embodiments, cartridge assembly 32 is a replaceable cartridge so that when all of fasteners 33 have been expelled, cartridge assembly 32 may be replaced with a replacement cartridge (not shown), in order to continue a surgical procedure. In another alternative, the jaw assembly 30 is incorporated into a loading unit that can be replaced after the fasteners are fired. The loading unit may have an elongated body portion that attaches to the elongated member 20.

In other embodiments, jaw assembly 30 may include a pair of jaw members that are configured to utilize laser energy, radio-frequency energy or any other suitable techniques to treat or join tissue. The laser and/or radio frequency energy may be used in combination with cartridge assembly 32 and anvil 34.

FIGS. 1-14 illustrate the components and operation the jaw assembly 30. Referring to FIG. 1, an exploded view of the jaw assembly 30 is shown. The jaw assembly 30 is adapted to apply a plurality of linear rows of staples or fasteners 33, which in embodiments may be of various sizes, e.g., about 30 mm in length. The jaw assembly 30 and/or the cartridge assembly can be replaceable so that 30 mm, 45 mm, or 60 mm long staple lines can be applied to tissue. Replaceable units for applying staples of different sizes are contemplated as well.

The jaw assembly 30 includes a carrier 31 having an elongate channel 110 having a base 112 and two parallel upstanding walls 114 and 116 which include several mounting structures, such as notches 139, for supporting the cartridge assembly 32 and the anvil 34. A longitudinal slot 111 extends through the elongate channel 110.

The carrier 31 also includes a plate cover 115 disposed on a bottom surface thereof. The plate cover 115 includes a plurality of knobs 117 configured to frictionally engage with corresponding apertures 119 disposed within the channel 112 of the carrier 31. The carrier 31 also includes a pair of tabs 107 and 109 disposed at a distal end thereof for coupling to a mounting portion 120.

With continuing reference to FIG. 1, the distal portion of channel 110 supports cartridge assembly 32 which contains a plurality of surgical staples or fasteners 33 and a plurality of corresponding ejectors or pushers 134. Actuation sled 140 having upstanding cam wedges 144, exerts a fastener driving force on the pushers 134, which drive the fasteners 33 from cartridge assembly 32, as described in more detail below. Cartridge assembly 32 is maintained within channel 110 by lateral struts 136 which frictionally engage the upper surfaces of channel walls 114 and 116, and the frictional engagement of housing tabs, such as tab 138, within notches 139. These structures serve to restrict lateral, longitudinal, and elevational movement of the cartridge assembly 32 within channel 110.

A plurality of spaced apart longitudinal slots 142 extend through cartridge assembly 32 to accommodate the upstanding cam wedges 144 of actuation sled 140. Slots 142 communicate with a plurality of transverse retention slots 146 within which the plurality of fasteners 33 and pushers 134 are respectively supported. The pushers 134 are secured by a pusher retainer 135 disposed below the cartridge assembly 32. The pusher retainer 135 supports and aligns the pushers 134 prior to engagement thereof by the actuation sled 140. During operation, as actuation sled 140 translates through cartridge assembly 32, the angled leading edges of cam wedges 144 sequentially contact pushers 136, causing the pushers to translate vertically within slots 146, urging the fasteners 134 therefrom. The cartridge assembly 32 also includes a longitudinal slot 185 to allow for the knife blade 174 to travel therethrough, as described in more detail below.

In certain embodiments, the cartridge 32 is removable from the jaw assembly. The pushers 134 are held in place by the retainer 135 and the retainer, which is attached to the cartridge by at least one proximal feature 201 and at least one distal feature 202, is removable with the cartridge. Hook shaped features on the retainer 135 are shown in FIG. 1, which illustrates a pair of distal features and a pair of proximal features. In use, the drive beam is refracted to a position proximal of the proximal ends of the cartridge and retainer, so that the removable assembly (the cartridge, pushers, and retainer) can be lifted out of the channel 110. In certain embodiments, the cartridge and channel form a detent connection so that the removable assembly is removable.

Figure 7:
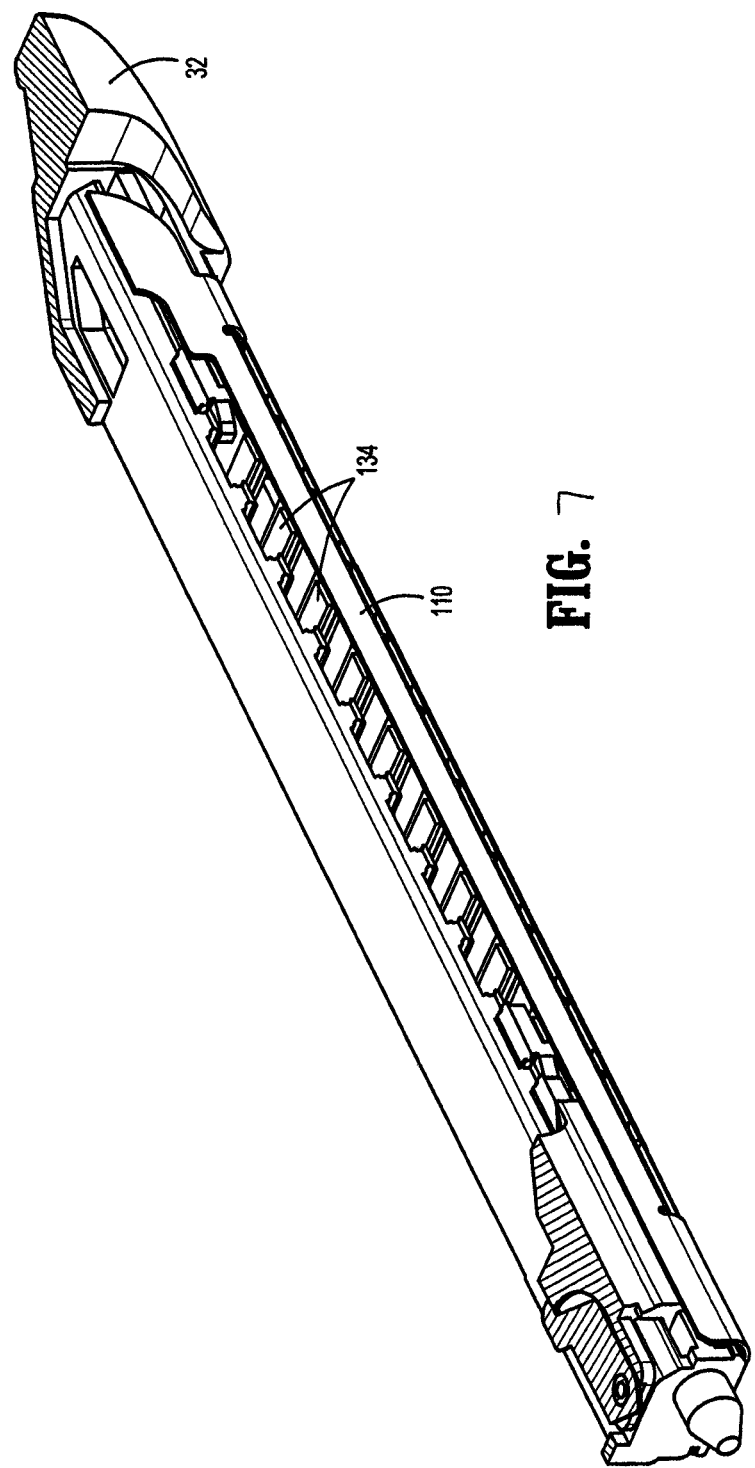
FIG. 7 is a bottom cross-sectional perspective view, with parts removed, of a jaw assembly in accordance with the embodiment of FIGS. 1 through 6.
Figure 8:
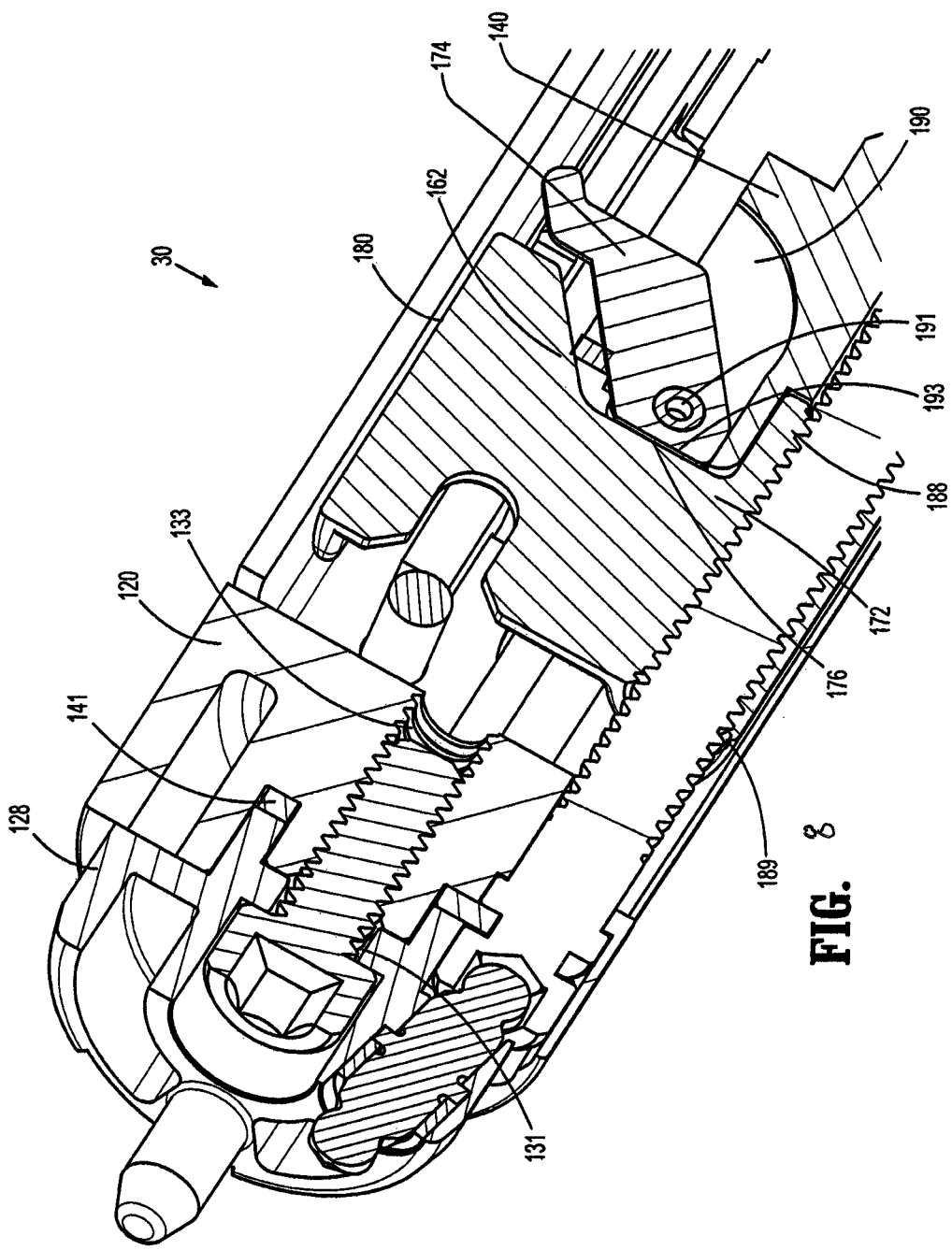
FIG. 8 is a perspective cross-sectional view of a portion of a jaw assembly in accordance with the embodiment of FIGS. 1 through 7.

With continuing reference to FIG. 1, the jaw assembly 30 includes an anvil cover 35 disposed over the anvil 34. The anvil cover 35 protects tissue from moving parts along the exterior of anvil 34. The anvil cover 35 includes opposed mounting wings 150 and 152 which are dimensioned and configured to engage detents 154 and 156 of the anvil 34, respectively. The mounting wings 150 and 152 also align the anvil 34 with the cartridge assembly 32 during closure as shown in FIGS. 7 and 8. The anvil 34 along with the cover 35 is configured to remain in an open configuration until closed, as described in more detail below. As shown in FIG. 1, the cover 35 includes a pair of actuating shoulders 157 and 159.

The anvil 34 and the carrier 31, including the cartridge assembly 32, are coupled to a mounting portion 120. The mounting portion 120 includes a pair of extensions 123 and 125, each having depressions 127 and 129, respectively. The depressions 127 and 129 are dimensioned and configured for insertion (e.g., frictionally fit) of a proximal portion of the carrier 31, including the tabs 107 and 109.

The mounting portion 120 includes a pair of openings 121 and 122 within the depressions 127 and 129. Each of the actuating shoulders 157 and 159 and the tabs 107 and 109 of the carrier 31 also include openings 157a, 159a, 107a, and 109a, respectively. A pivot pin 117, or a pair of pins, passes through the openings 121, 122, 157a, 159a, 107a, and 109a.

Figure 5:
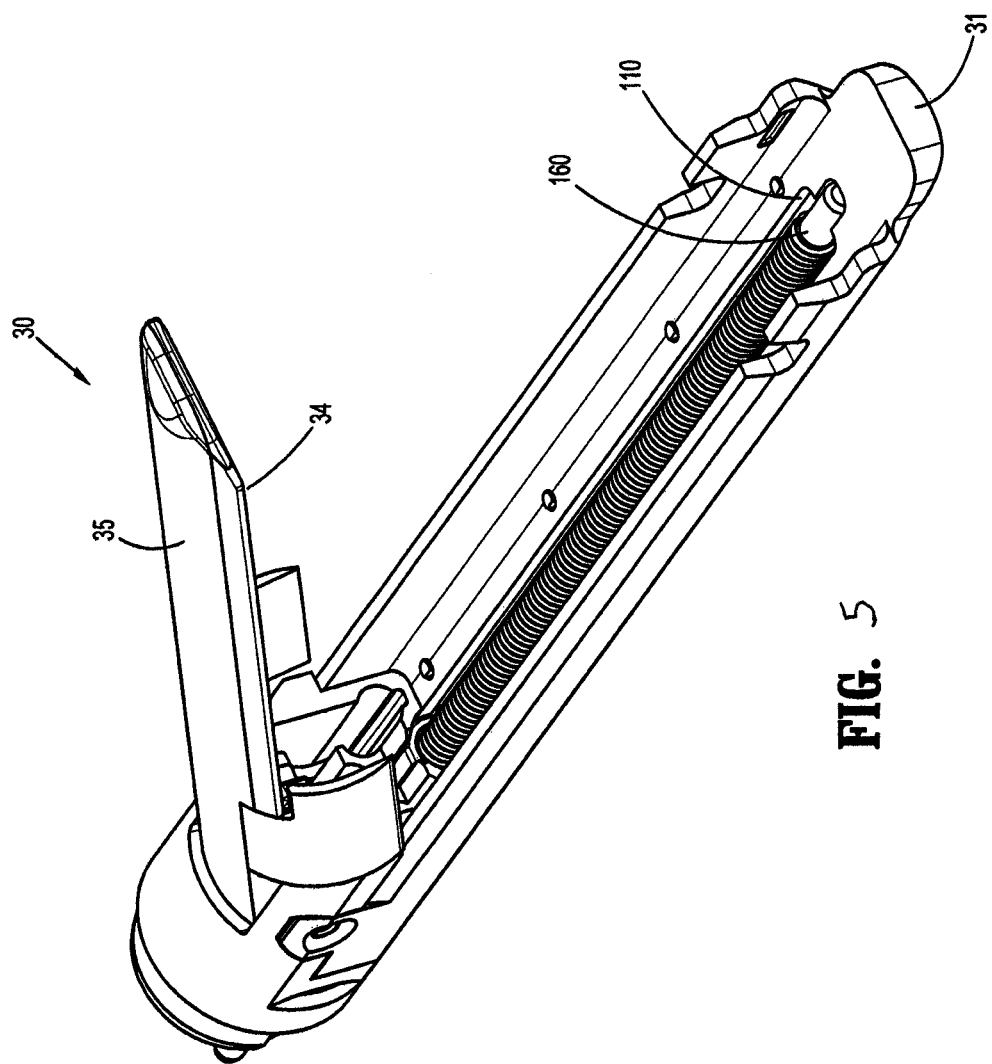
FIG. 5 is a front, perspective view of a jaw assembly in accordance with the embodiment of FIGS. 1 through 4.
Figure 6:
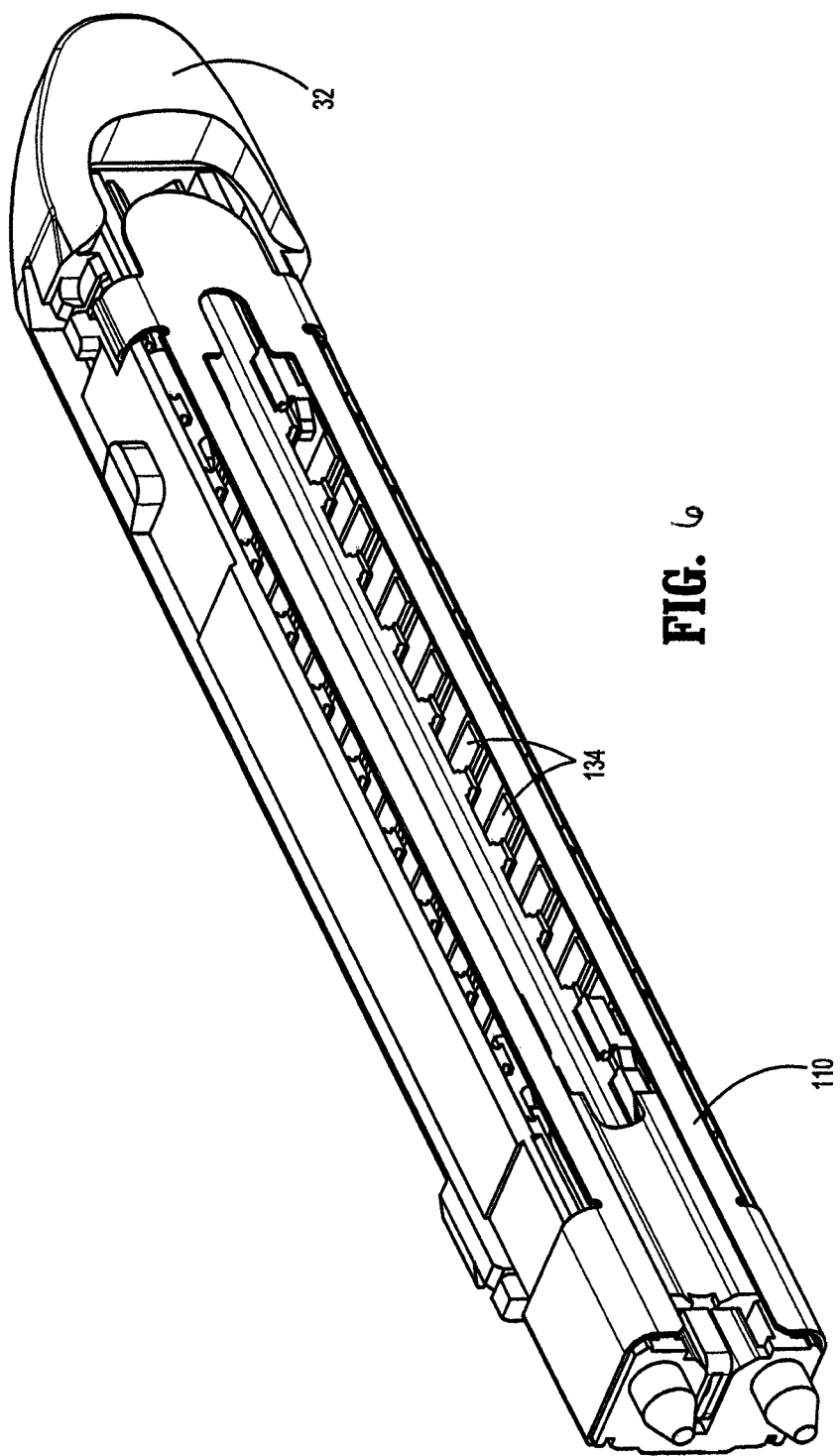
FIG. 6 is a bottom perspective view, with parts removed, of a jaw assembly in accordance with the embodiment of FIGS. 1 through 5.

As shown in FIGS. 6, 18 and 19, biasing members 158a and 158b, which are shown as coil springs, are secured within the mounting portion 120. The biasing members 158a and 158b bear against internal bearing surfaces defined within mounting portion 120 to bias anvil 34 into a normally open position wherein the interior fastener forming surface 39 thereof is spaced from cartridge assembly 32. In particular, as described above, the anvil 34 includes actuating shoulders 157 and 159 disposed at a proximal end thereof. Each of the actuating shoulders 157 and 159 includes contact surfaces 157b and 159b, respectively. The contact surfaces 157b and 159b abut the biasing members 158a and 158b, respectively, pushing the anvil 34 into the open position as shown in FIG. 5. As the anvil 34 is closed, the biasing members 158a and 158b are compressed within the mounting portion 120.

With reference to FIGS. 1 and 8, a coupling member 128 is coupled to the proximal end of the mounting portion 120. The coupling member 128 includes an axial bore 131 defined therethrough. The mounting portion 120 also includes an axial bore 133 defined therein, which is aligned with the axial bore 131 of coupling member 128 when the coupling member 128 is coupled thereto. The bores 131 and 133 are threaded and are dimensioned and configured to be interconnected by a bolt 135.

Figure 2:
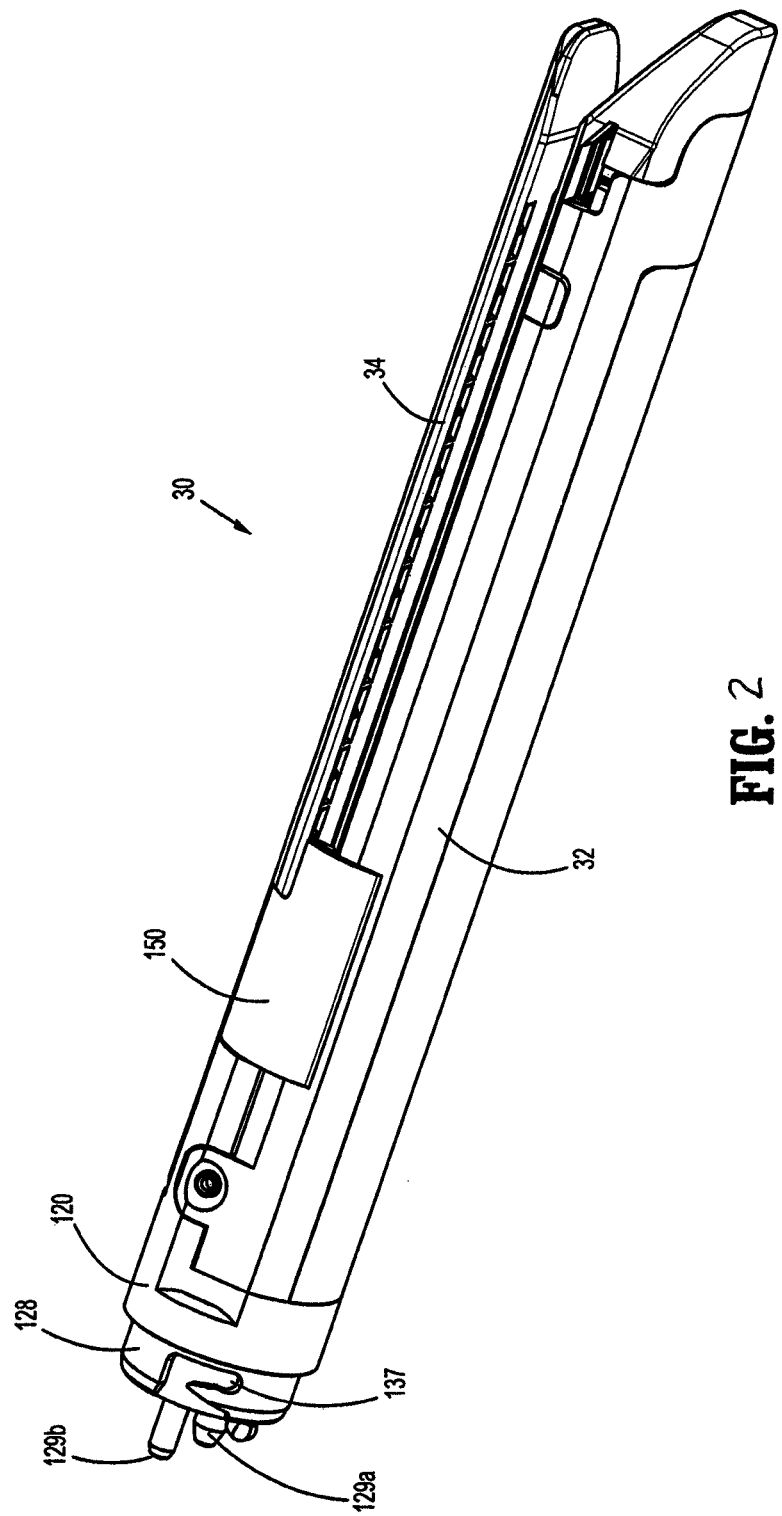
FIG. 2 is a side, perspective view of a jaw assembly in accordance with the embodiment of FIG. 1.
Figure 3:
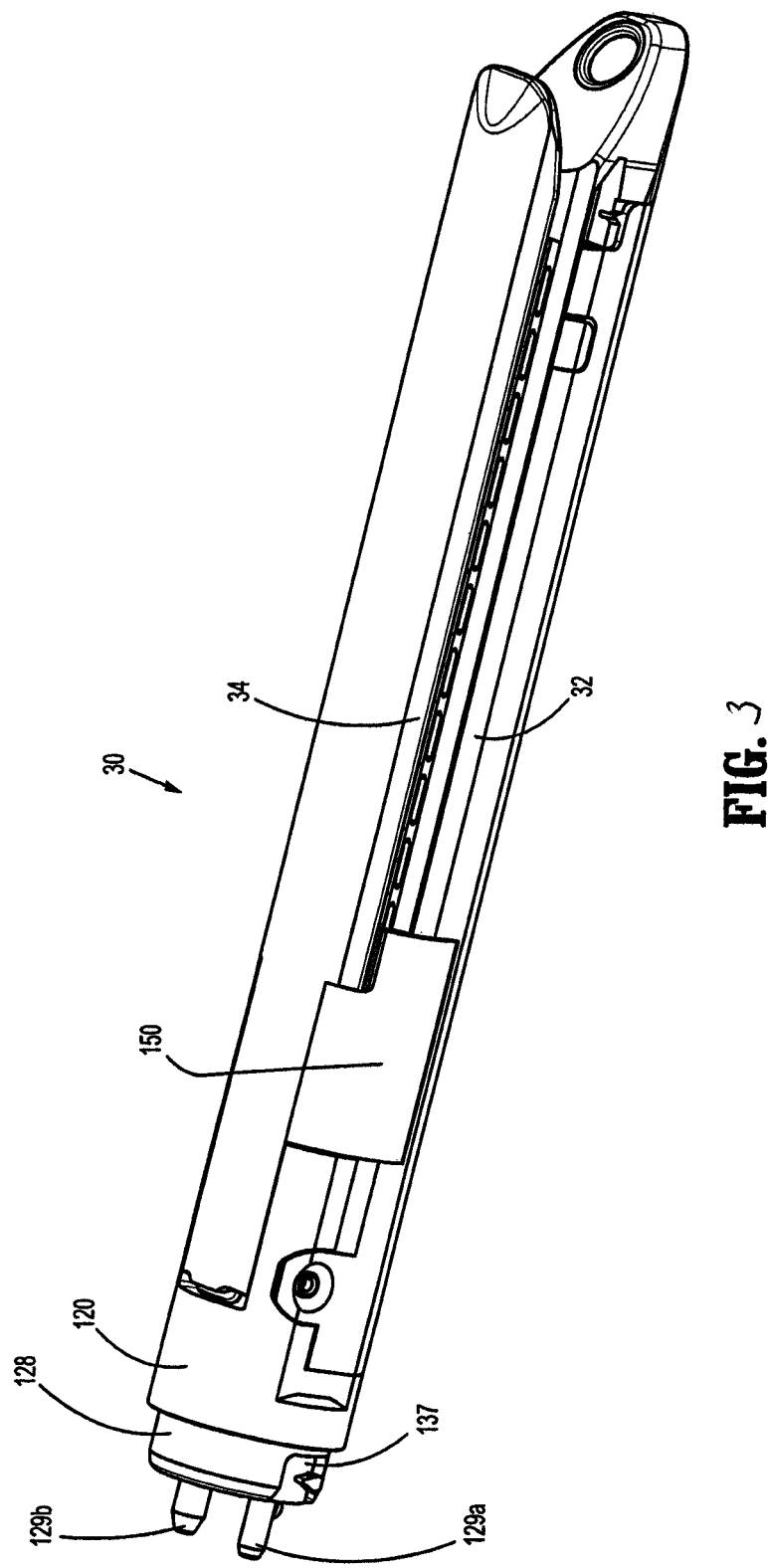
FIG. 3 is a top, perspective view of a jaw assembly in accordance with the embodiment of FIGS. 1 and 2.
Figure 4:
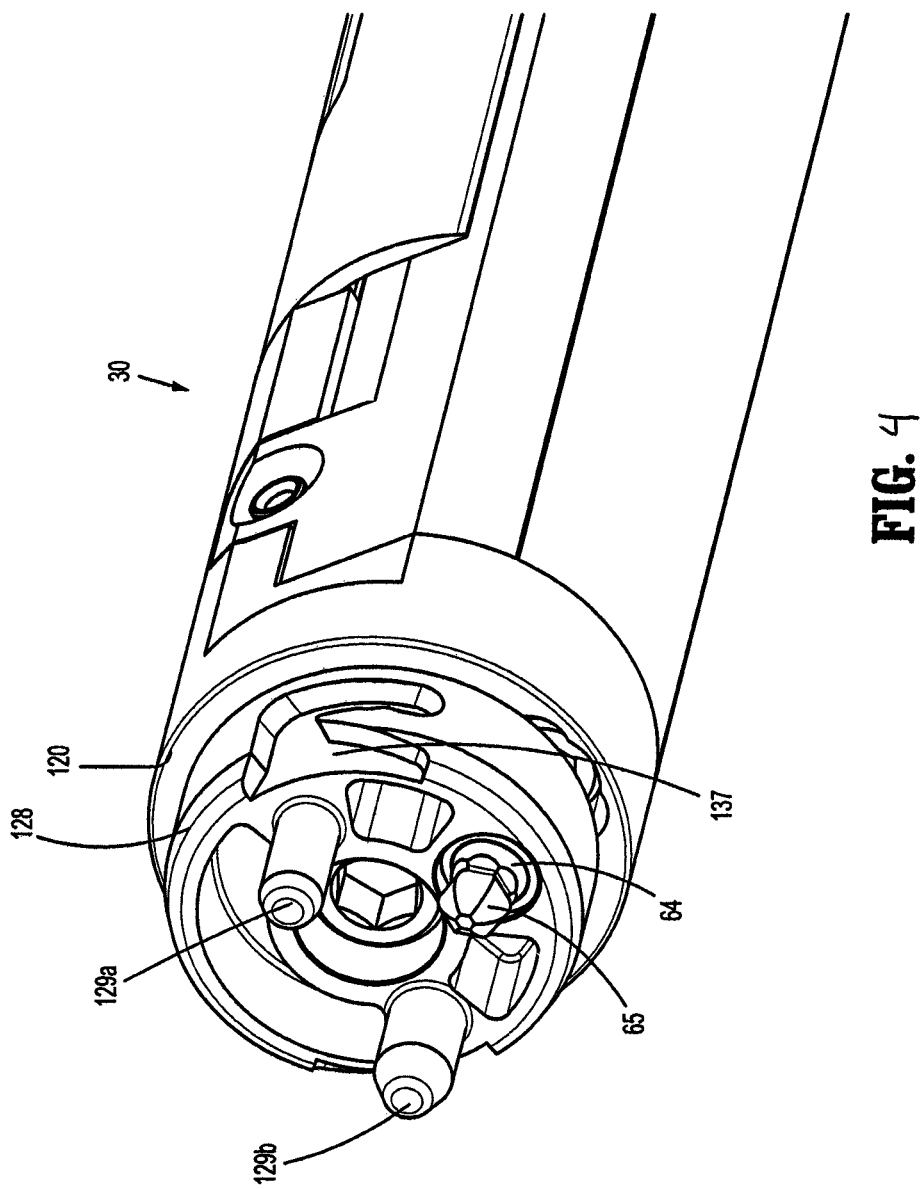
FIG. 4 is a rear, perspective view of a jaw assembly in accordance with the embodiment of FIGS. 1 through 3.

With continued reference to FIG. 2, the coupling member 128 includes a J-shaped slot 137, and one or more alignment shafts 129a and 129b. The alignment shafts 129a and 129b along with the slot 137 are used to align and couple the jaw assembly 30 to the distal end 24 of the elongated member 20. The shafts 129a and 129b may align the elongated member 20 with the jaw assembly 30 and the slot 137 may define a conventional bayonet-type coupling which facilitates quick and easy engagement and removal of the jaw assembly 30 from the instrument 10 during a surgical procedure. Once engaged in the distal end 24 of the elongated portion 20, the drive mechanism, e.g., actuation shaft 55, of the instrument 10 is coupled to a drive shaft 64 of the jaw assembly 30.

As seen in FIG. 1, jaw assembly 30 further includes an axial drive screw 160 for transmitting the rotational drive forces exerted by the drive shaft in the handle assembly to actuation sled 140 during a stapling procedure. The drive shaft 64 is disposed within the mounting portion 120 and includes a proximal portion 65 and a distal portion 67. The proximal portion 65 is configured to be engaged by the actuation shaft extending from the instrument 10, and the distal portion 67 is dimensioned and configured to engage the drive screw 160. The actuation shaft includes a distal engagement portion. The engagement portion includes a multi-faceted or non-circular female connection (e.g., hexagonal) which is dimensioned and configured to engage the proximal portion 65 of the drive shaft 64.

The proximal and distal portions 65 and 67 are shaped as multi-faceted or non-circular male connections. The drive shaft 64 also includes a bushing 69 disposed centrally thereon. The bushing 69 allows the drive shaft 64 to rotate about its longitudinal axis A-A. The drive shaft 64 is secured within the mounting portion 120 via a frictionally fit washer 71, which prevents the drive shaft 64 from sliding out of the mounting portion 120.

Figure 9:
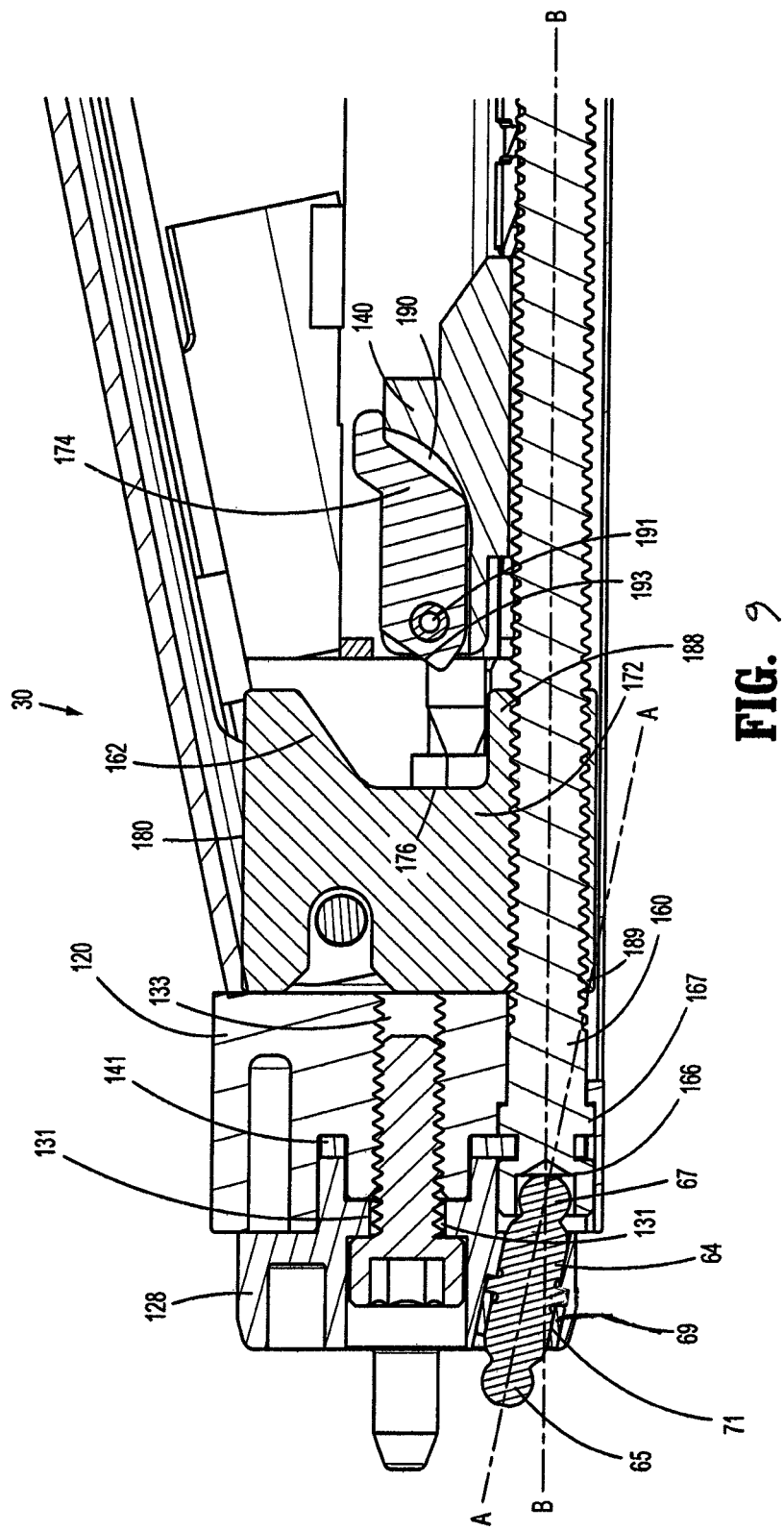
FIG. 9 is a side cross-sectional view of a portion of a jaw assembly in accordance with the embodiment of FIGS. 1 through 8.
Figure 10:
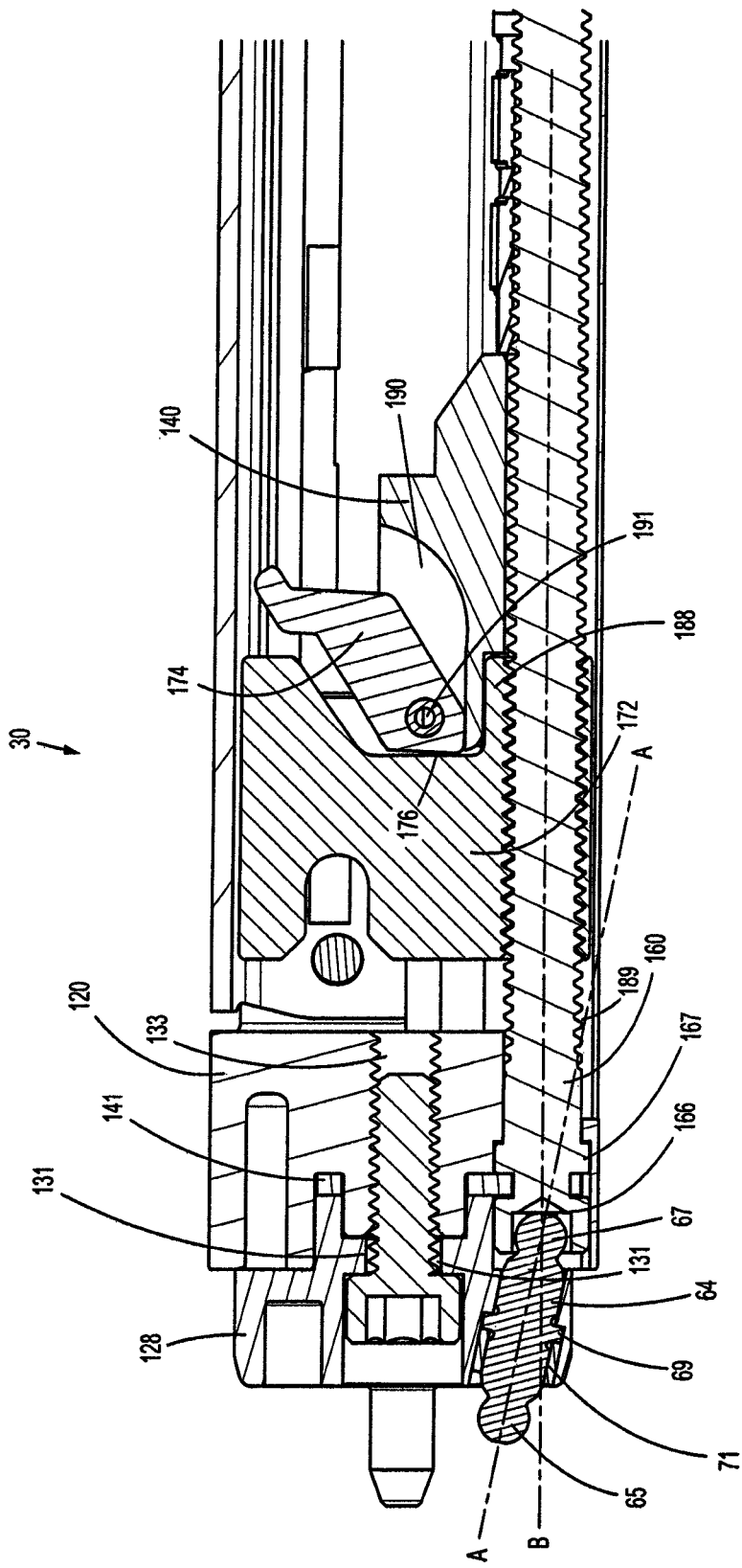
FIG. 10 is a side cross-sectional view of a jaw assembly in accordance with the embodiment of FIGS. 1 through 9.

Drive screw 160 includes a threaded portion 160a and a proximal engagement portion 166. Engagement portion 166 includes a multi-faceted or non-circular female connection 164 (e.g., hexagonal) which is dimensioned and configured to engage the distal portion 67 of the drive shaft 64. The drive screw 160 is disposed within the longitudinal slot 111 of the carrier 31 as shown in FIGS. 6 and 10. The drive screw 160 is rotatably secured at its engagement portion 166 via a thrust plate 141. The thrust plate 141 is disposed between the coupling member 128 and the mounting portion 120 and is fitted over a portion of the coupling member 128, as shown in FIG. 9. In particular, the thrust plate 141 includes a pair of teeth 143a and 145a that engage the drive screw 160 between the engagement portion 166 and a protrusion 167, thereby preventing lateral, longitudinal, and elevational movement and allowing only for rotation of the drive screw 160 about a longitudinal axis B-B. As described above, the drive shaft 64 is disposed within the mounting portion 120 off-axis with respect to the drive screw 160. The longitudinal axis A-A defined by the drive shaft 64 is at a non-parallel (e.g., non-zero angle) angle with respect to the longitudinal axis B-B defined by the drive screw 160.

With reference to FIGS. 1 and 9, a drive beam 162 is also disposed within the jaw assembly 30. The drive beam 162 includes a vertical support strut 172 and an abutment surface 176 which engages the central support wedge 145 (FIG. 1) of actuation sled 140. The drive beam 162 also includes a cam member 180 disposed on top of the vertical support strut 172. Cam member 180 is dimensioned and configured to engage and translate with respect to an exterior camming surface 182 of anvil 34 to progressively clamp the anvil against body tissue during firing.

A longitudinal slot 184 extends through the anvil 34 to accommodate the translation of the vertical strut 172. In embodiments, the anvil cover 35 is secured to an upper surface of anvil 34 to form a channel therebetween. This allows the cam member 180 to travel in between the cover 35 and anvil 34 during firing.

The drive beam 162 includes a retention foot 188 having a threaded bore 189 defined therethrough. The drive screw 160 is threadably coupled to the drive beam 162 through the bore 189, such that as the drive screw 160 is rotated, the drive beam 162 travels in a longitudinal direction along the axis B-B.

As the drive screw 160 is rotated in a clock-wise direction, the drive beam 162 travels in a distal direction closing the anvil 34 as the cam member 180 pushes down on the camming surface 182 thereof. The drive beam 162 also pushes the sled 140 in the distal direction, which then engages the pushers 134 via the cam wedges 144 to eject the fasteners 33.

Figure 11:
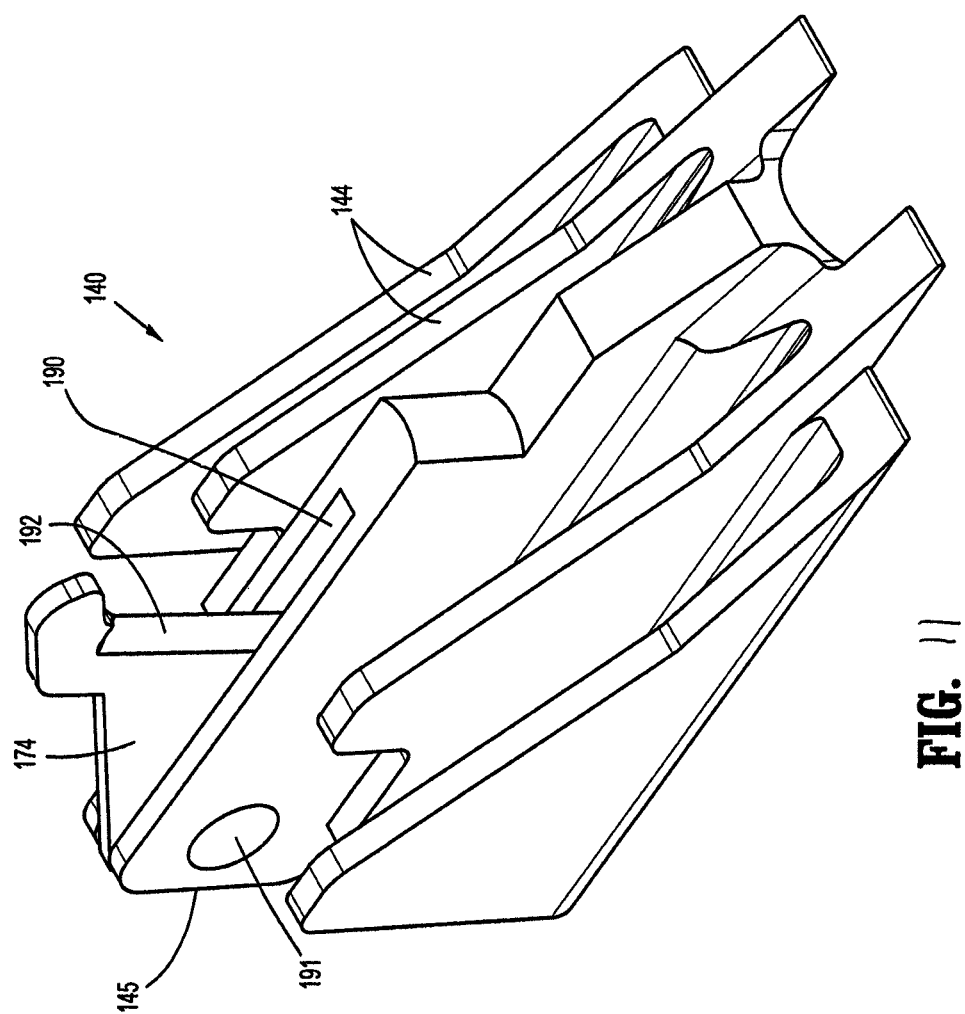
FIG. 11 is a perspective view of an actuation sled of a jaw assembly in accordance with the embodiment of FIGS. 1 through 10.
Figure 12:
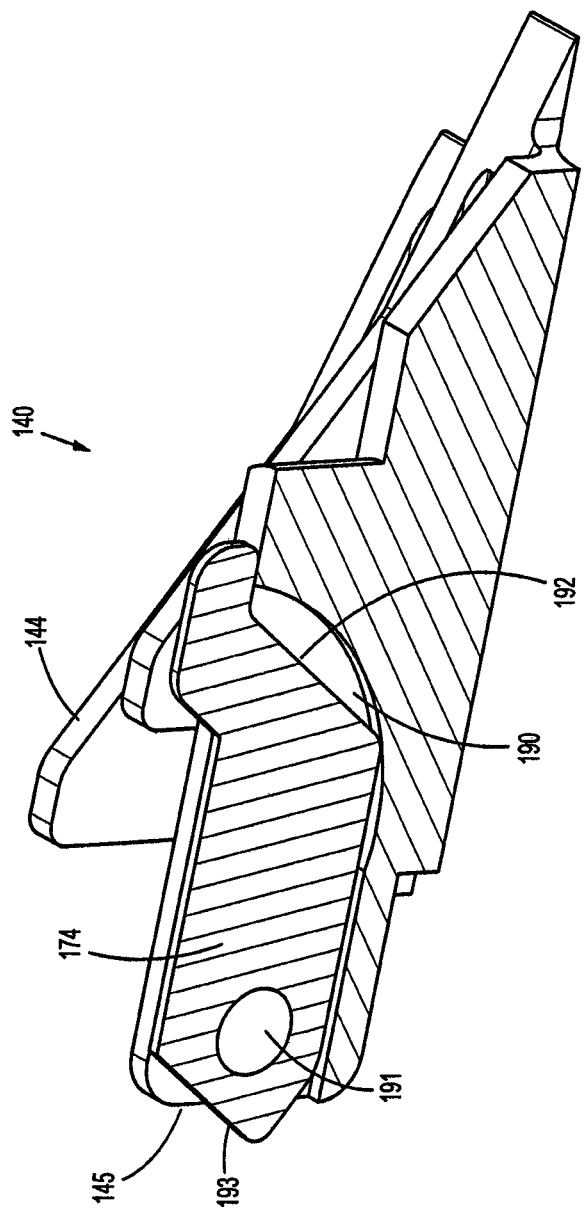
FIG. 12 is a perspective cross-sectional view of a jaw assembly in accordance with the embodiment of FIGS. 1 through 11.
Figure 13:
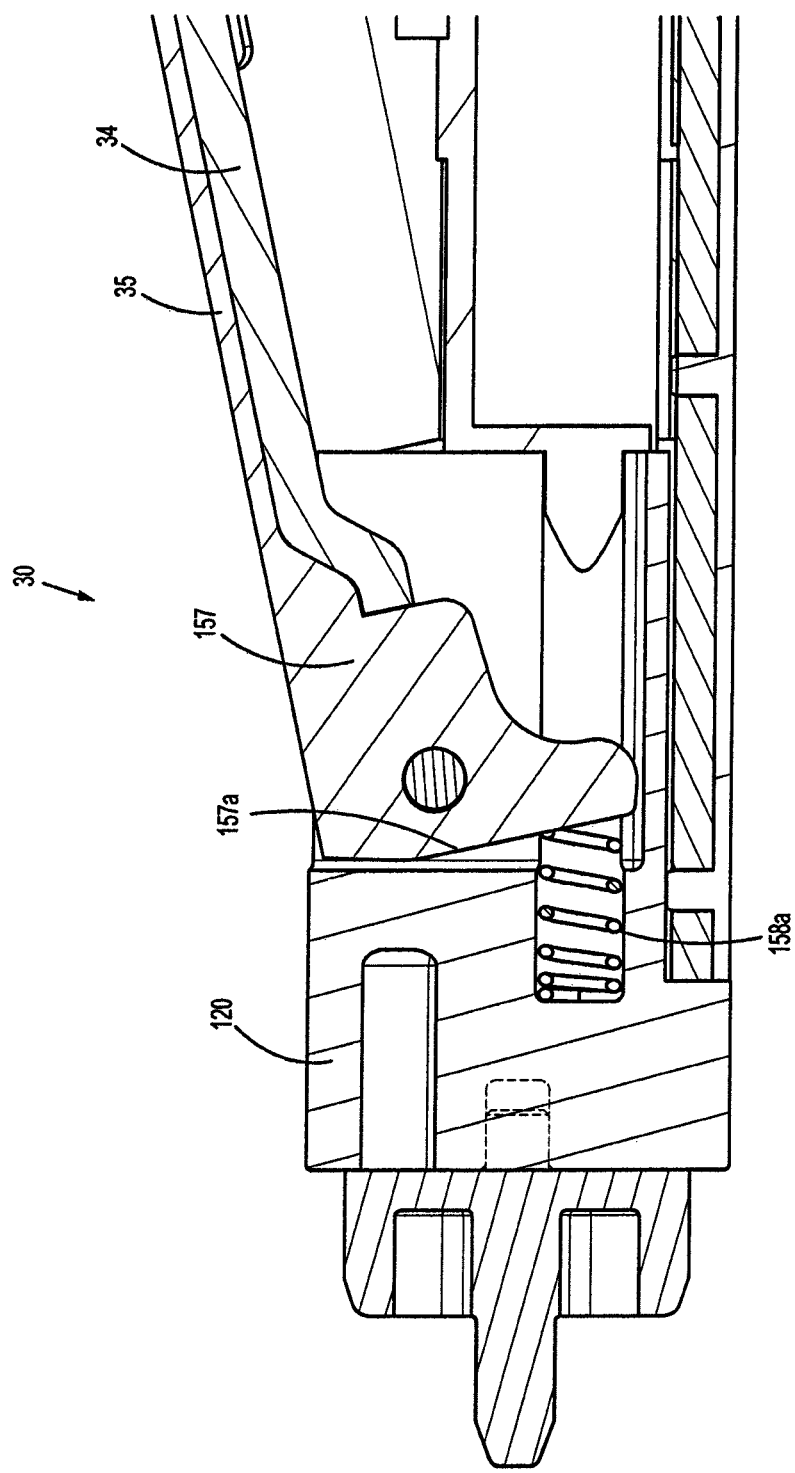
FIG. 13 is a side cross-sectional view of a portion of a jaw assembly in accordance with the embodiment of FIGS. 1 through 12.
Figure 14:
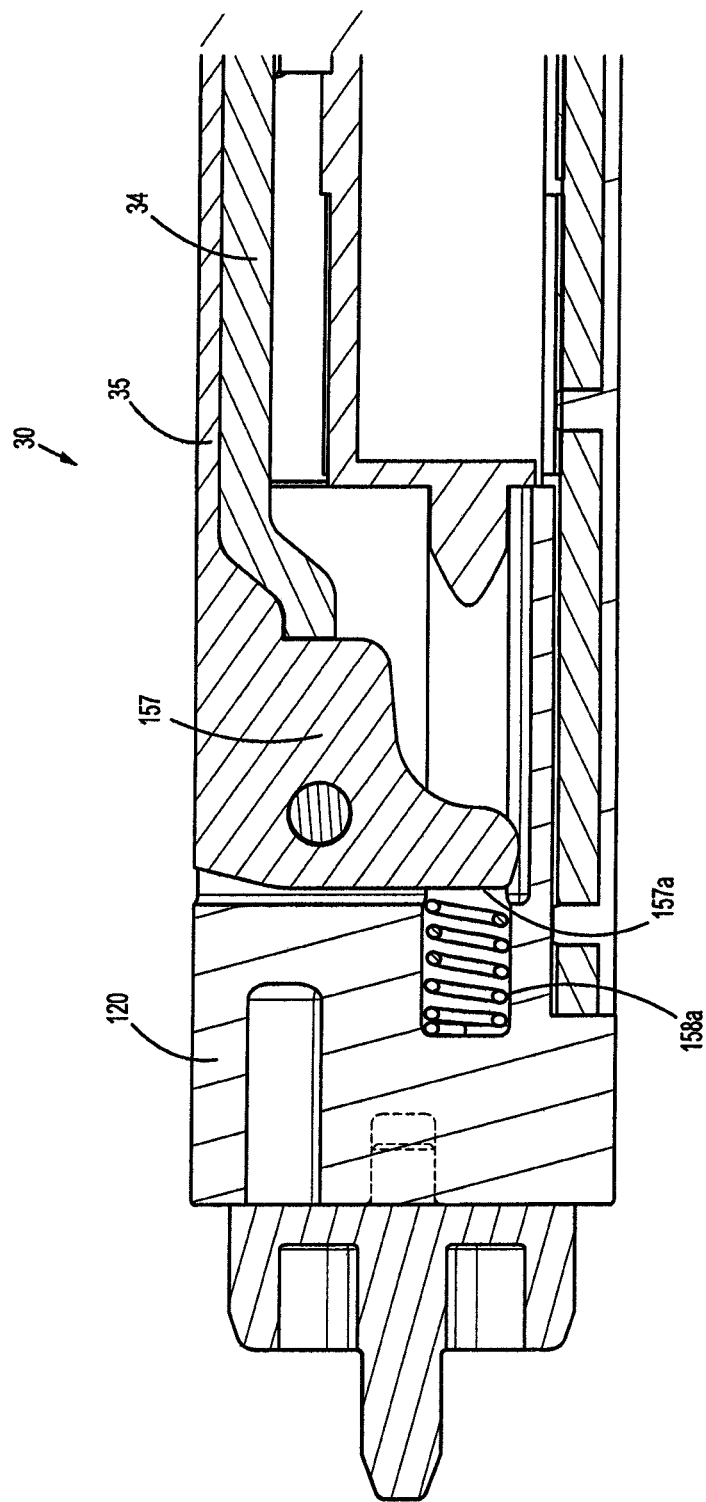
FIG. 14 is a side cross-sectional view of a portion of a jaw assembly in accordance with the embodiment of FIGS. 1 through 13.

The sled 140 also includes a knife blade 174 for transecting the fastened tissue. The knife blade 174 travels slightly behind actuation sled 140 during a stapling procedure to form an incision between the rows of fastener body tissue. As shown in FIG. 11, the sled 140 includes a centrally disposed slit 190 for housing the knife blade 174, which is pivotally coupled to the sled 140 via a pin 191. The knife blade 174 includes a blade portion 192 at a distal end and an actuating surface 193 disposed at a proximal end (see FIG. 12). The knife blade 174 pivots about the pin 191 from a concealed position in which the knife blade 174 is fully submerged within the slit 190, as shown in FIGS. 9 and 12, and a raised position in which the knife blade 174 is in a deployed upright position extending through the longitudinal slot 185, as shown in FIG. 10.

As the drive beam 162 is driven in the distal direction, the abutment surface 176 of the vertical strut 172 comes in contact with a actuating surface 193 of knife body 174, thereby pivoting the knife blade 174 about the pin 191 and raising the blade portion 192 from the slit 190 and into the longitudinal slot 185, as shown in FIGS. 9 and 10. As the drive beam 162 is continually driven in the distal direction, the abutment surface 176 maintains contact with the knife blade 174, thereby pushing the sled 140 in the distal direction to eject the fasteners 33 and simultaneously dissect tissue with the blade portion 192. The knife blade 174 and the drive beam 162 travel through the knife slot 38 thereby fastening and severing tissue. In particular, the knife slot 38 is formed by the longitudinal slots 184 and 185 defined in the anvil 34, the anvil cover 35, and the cartridge assembly 32, respectively. The drive beam 162 closes the anvil as it is driven in the distal direction and also pushes the sled 140, which, in turn, ejects the fasteners 33 ahead of the knife blade 174 that is pivoted into the upright position.

The jaw assembly may be removably attached to a elongated shaft member that is flexible, or rigid, or has rigid and flexible portions. In this way, the user of the surgical instrument can select the type of elongated shaft member for the particular procedure to be performed. In addition, the handle assembly is removably attached to the elongated shaft member so that the shaft members can be interchanged. The handle assembly desirably has a housing, a motor, a drive shaft, and a controller. The controller may be configured to interact with the shaft and/or jaw assembly to modify the operation of the handle assembly to correspond to the particular jaw assembly and/or shaft member attached to the handle assembly.

Each of the embodiments described above are provided for illustrative purposes only and it is within the concept of the present disclosure to include modifications and varying configurations without departing from the scope of the disclosure that is limited only by the claims included herewith.

The invention claimed is:

1. A surgical instrument comprising:
   a handle assembly including a housing;
   an elongated body extending distally from the handle assembly; and
   a jaw assembly adjacent a distal end of the elongated body, the jaw assembly including:
      a cartridge assembly including a plurality of fasteners and a longitudinal slot defined therein;
      an anvil having a fastener forming surface thereon, the cartridge assembly and anvil being mounted for movement with respect to one another between an open position and a closed position in close cooperative alignment for clamping tissue;
      an actuation sled supported within the cartridge assembly, the actuation sled being movable to urge the plurality of fasteners from the cartridge;
      a knife blade mounted to the actuation sled;
      a drive beam including a vertical support strut and a cam member supported on the vertical support strut, the cam member being positioned to translate relative to the anvil to maintain the anvil in the closed position during firing of the fasteners, the vertical support strut being positioned to abut the actuation sled; and
      a drive screw supported within the cartridge assembly, the drive screw having a threaded portion, wherein the drive beam is threadably coupled to the threaded portion of the drive screw such that rotation of the drive screw imparts longitudinal movement of the drive beam.

2. The surgical instrument according to claim 1, wherein the knife blade is pivotably mounted to the actuation sled for pivotable movement in relation to the sled between a concealed position in which the knife blade is disposed within the actuation sled and a raised position in which the knife blade extends through the longitudinal slot.

3. The surgical instrument according to claim 2, wherein the knife blade has an actuating surface that is arranged to be contacted by the vertical support strut.

4. The surgical instrument according to claim 3, wherein the drive screw defines a longitudinal axis and the drive shaft is disposed off-axis in relation to the drive screw.

5. The surgical instrument according to claim 1, wherein the jaw assembly further includes:
   a mounting portion coupled to the cartridge assembly and the anvil, the anvil being pivotally mounted to the mounting portion for pivotal movement in relation to the cartridge.

6. The surgical instrument according to claim 5, wherein the anvil includes a pair of actuating shoulders disposed at a proximal end thereof.

7. The surgical instrument according to claim 6, wherein the mounting portion includes a pair of biasing members biased against the actuating shoulders for pushing the anvil into the open position.

8. The surgical instrument according to claim 1, further comprising a camera mounted on the at least one of the cartridge assembly and the anvil.

9. The surgical instrument according to claim 8, wherein the camera is mounted on the anvil.

10. A surgical instrument comprising:
    a handle assembly including a housing and an actuator;
    an elongated body extending distally from the handle assembly;
    a motor disposed at least partially within the housing;
    an actuation shaft mechanically engaged with the motor;
    a jaw assembly adjacent a distal end of the elongated body, the jaw assembly including:
       a cartridge assembly including a plurality of fasteners and a longitudinal slot defined therein;
       an anvil having a fastener forming surface thereon, the cartridge assembly and anvil being mounted for pivotal movement with respect to one another between an open position and a closed position for clamping tissue;
an actuation sled supported within the cartridge assembly, the actuation sled being movable to urge the plurality of fasteners from the cartridge;
a knife blade mounted to the actuation sled;
a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled to translate the actuation sled; and
a drive screw supported within the cartridge assembly, the drive screw having a threaded portion, wherein the drive beam is threadably coupled to the threaded portion of the drive screw such that rotation of the drive screw imparts longitudinal movement of the drive beam.

11. The surgical instrument according to claim 10, wherein the knife blade is pivotally mounted to the sled for movement in relation to the sled between a concealed position in which the knife blade is disposed within the actuation sled and a raised position in which the knife blade extends through the longitudinal slot.

12. The surgical instrument according to claim 10, wherein the jaw assembly further includes:
a mounting portion coupled to the cartridge assembly and the anvil, the anvil being pivotally mounted to the mounting portion for pivotal movement in relation to the cartridge.

13. The surgical instrument according to claim 12, wherein the jaw assembly further includes:
a drive shaft disposed within the mounting portion, the drive shaft mechanically coupling the drive screw to the actuation shaft, wherein the drive shaft transfers rotational motion of the actuation shaft to the drive screw.

14. The surgical instrument according to claim 13, wherein the drive shaft is coupled off-axis to the drive screw.

15. The surgical instrument according to claim 10, wherein the anvil includes a pair of actuating shoulders disposed at a proximal end thereof.

16. The surgical instrument according to claim 15, wherein the mounting portion includes a pair of biasing members biased against the actuating shoulders for pushing the anvil into the open position.

17. The surgical instrument according to claim 10, further comprising a camera mounted on the at least one of the cartridge assembly and the anvil.

18. The surgical instrument according to claim 17, wherein the camera is mounted on the anvil.

19. A jaw assembly comprising:
a cartridge assembly including a plurality of fasteners and a longitudinal slot defined therein;
an anvil having a fastener forming surface thereon and pivotally mounted in relation to the cartridge assembly for pivotal movement between an open position having a distal end spaced from the cartridge assembly and a closed position in close cooperative alignment with the fastener cartridge;
an actuation sled supported within the cartridge assembly, the actuation sled being movable to urge the plurality of fasteners from the cartridge;
a knife blade pivotally mounted to the actuation sled for pivotal movement in relation to the sled between a closed position in which the knife blade is disposed within the actuation sled and a deployed position in which the knife blade extends through the longitudinal slot; and
a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled and the knife blade to translate the actuation sled and to pivot the knife blade from the closed position into the deployed position.

20. The jaw assembly according to claim 19, further comprising:
a drive screw supported within the cartridge assembly, the drive screw having a threaded portion, wherein the drive beam is threadably coupled to the threaded portion of the drive screw such that rotation of the drive screw imparts longitudinal movement of the drive beam.

21. The jaw assembly according to claim 20, further comprising:
a drive shaft mechanically coupling the drive screw to an actuation shaft, wherein the drive shaft transfers rotational motion of the actuation shaft to the drive screw.

22. The jaw assembly according to claim 21, wherein the drive shaft is coupled off-axis to the drive screw.

23. The jaw assembly according to claim 19, further comprising:
a mounting portion coupled to the cartridge assembly and the anvil, the anvil being pivotally mounted to the mounting portion for pivotal movement in relation to the cartridge.

24. The jaw assembly according to claim 23, wherein the anvil includes a pair of actuating wings disposed at a proximal end thereof, the mounting portion includes a pair of biasing members biased against the actuating wings for pushing the anvil into the open position.

* * * * *